US006645487B2

(12) United States Patent
Cezayirli et al.

(10) Patent No.: US 6,645,487 B2
(45) Date of Patent: Nov. 11, 2003

(54) METHOD FOR STIMULATING AN IMMUNE RESPONSE (76) Inventors: Cem Cezayirli, 801 Princeton Ave. Suite 310, Birmingham, AL (US) 35211; Mel Silvers, 18970 NE. 21st Ave., North Miami Beach, FL (US) 33179

( * ) Notice: Subject to any disclaimer, the term of this patent is extended or adjusted under 35 U.S.C. 154(b) by 214 days.

(21) Appl. No.: 09/746,632

(22) Filed: Dec. 20, 2000

(65) Prior Publication Data

US 2001/0001066 A1 May 10, 2001

Related U.S. Application Data (63) Continuation of application No. 09/017,842, filed on Feb. 3, 1998, now Pat. No. 6,251,665.
(60) Provisional application No. 60/042,110, filed on Mar. 26, 1997, provisional application No. 60/038,736, filed on Feb. 14, 1997, and provisional application No. 60/037,435, filed on Feb. 7, 1997.

(51) Int. Cl.$^7$ .................. A01N 63/00; A01N 65/00; C12N 5/00; C12N 5/02; C12N 5/08; C12N 5/04; C07K 1/00; C07K 14/00

(52) U.S. Cl. ............... 424/93.1; 424/93.7; 435/325; 435/326; 435/372; 435/372.3; 435/373; 435/377; 435/385; 435/386; 530/351

(58) Field of Search .................. 424/93.1, 93.7; 435/325, 326, 372, 372.3, 373, 377, 385, 386; 530/351

(56) References Cited

U.S. PATENT DOCUMENTS

| | | | |
|---|---|---|---|
| 5,316,920 A | 5/1994 | Tedder et al. |
| 5,648,219 A | 7/1997 | MacKay et al. |
| 5,831,068 A | 11/1998 | Nair et al. |
| 5,843,648 A | 12/1998 | Robbins et al. |
| 5,853,719 A | 12/1998 | Nair et al. |
| 5,994,126 A | 11/1999 | Steinman et al. |

OTHER PUBLICATIONS

Markowicz, J. Clinical Inv., vol. 85, Mar. 1990, p. 99–61
Caux, Blood, vol. 75 (12), Jun. 1990, p. 2292–2298.
Peters, Adv. Exp. Med. Biol., vol. 329, 1993, p. 275–280.
Cohen, Cancer Res., vol. 54(4), Feb. 1993, p. 1055–1058.
Jaffe, Ped.Path., vol. 13, Nov.–Dec. 1993, p. 821–835.
Cohen, Eur. J. Immunol., vol. 24(2), Feb. 1994, p. 315–319.
Romani, J. Exp.Med., vol. 180, Jul. 1994, p. 83–93.
Santiago–Schwarz, Stem Cells, vol. 13, Mar. 1995, p. 186–197.
Galy, Immunity, vol. 3, Oct. 1995, p. 459–473.
Alijagic, Eur. J. Immunol., vol. 25(11), Nov. 1995, p. 3100–3107.
van Lochen, Hum. Immunol., vol. 44(3), Nov. 1995, p. 181–188.
Sienna, Exp. Hematol., vol. 23(14), Dec. 1995, p. 1643–1649.
Garcia, Plata, Invasion & Metastisis, 15 (3–4), 1995, p. 125–134.
Tiemessen, Adv. Exp. Med. Biol., vol. 378, 1995, p. 85–87.
Tjoa, Prostate, vol. 28(1), Jan. 1995, p. 65–69.
Thomas, Arth. Rheumatism, vol. 39(1), Feb. 1996, p. 183–190.
Cameron, J. Leuk. Biol. vol. 59(2), Feb. 1996, p. 158–171.
Zhou, Prac. Natl. Acad. Sci., vol. 93, Mar. 1996, p. 2558–2592.
Thomas, J. Immunol., vol. 156(8), Apr. 1996, p. 3074–3086.
Saraya, Br. J., Haemotol., vol. 93, May 1996, p. 258–264.
McLellan, Eur. J. Immunol., vol. 26(6), Jun. 1996, p. 1204–1210.
Res, Blood, vol. 87(12), Jun. 1996, p. 5196–5206.
Cella, J. Exp. Med., vol. 184(1), Aug. 1996, p. 747–752.
Steinman, Exp. Hematol, vol. 24, Aug. 1996, p. 859–862.
Caux, J. Exp.Med., vol. 184, Aug. 1996, p. 695–706.
Bender, J. Immunol. Methods, vol .196, Sep. 1996, p. 121–135.
Pickl, J. Immunol., vol. 157, Nov. 1996, p. 3850–3854.
Van Elsas, Eur. J. Immunol., vol. 26, 1996, p. 1683–1689.
Romani, J. Immunol. Methods, vol. 196, 1996, p. 137–151.
Morse, Ann. Surg., vol. 226(1), Jul. 1997, p. 6–16.
Thomas R. Lipsky PE. Arthritis & Rheumatism, Feb. 1996., 39(2):183–90.
Cella M., et al. Journal of Experimental Medicine, Aug. 1, 1996, 184(2):747–52.
Garcia–Plata D., et al, Invasion & Metastasis, 1995, 15(3–4):125–34.
Tiemessen CT., et al, Advances in Experimental Medicine & Biology, 1995, 378:85–7.
McLellan A.D., et al, European Journal of Immunology, Jun. 1996, 26(6):1204–10.

(List continued on next page.)

*Primary Examiner*—Christina Chan
*Assistant Examiner*—Michail Belyavskyi
(74) *Attorney, Agent, or Firm*—Bradley Arant Rose & White, LLP (57) ABSTRACT A method is described whereby dendritic cells derived from the CD34+ and CD 34-hematopoietic cell lineages are directed to become programmable antigen presenting cells. The programmed cells may be pulsed with tumor cell RNA or tumor cell RNA expression products. The protocol provides for directing the maturation of dendritic cells to become antigen presenting cells. The protocol further provides for isolating tumor cell RNA from biopsy material that has been prepared in paraffin block storage. The directed dendritic cell is provided with a plurality of tumor markers by using tumor RNA in toto, the poly A+RNA fraction or the expression product of such RNA. Once activated the dendritic cells are incubated with T4 and T8 lymphocytes to stimulate and sensitize the T lymphocytes which upon introduction either into a donor host or a nondonor recipient will provide immune response protection.

7 Claims, 4 Drawing Sheets

OTHER PUBLICATIONS van Elsas A., et al, European Journal of Immunology, Aug. 1996, 26(8):1683–9.

Thomas R., et al, Journal of Immunology, Apr. 15, 1996, 156(8):3074–86.

Steinman R.M., Experimental Hematology, Jul. 1996, 24(8):859–62.

Cameron P., et al, Journal of Leukocyte Biology, Feb. 1996, 59(2):158–71.

van Lochem E.G., et al, Hum Immunology, Nov. 1995, 44(3):181–8.

Tjoa B., et al, Prostate, Jan. 1996, 28(1):65–9.

Cohen, Cancer Res., vol. 54(4), Feb. 1993, p. 1055–1058.

Galy, Immunity, vol. 3, Oct. 1995, p. 459–473.

Romani, J. Immunol. Methods, vol. 196, 1996, p. 137–151.

New Dendritic Cells Invented for Creation of Cancer Vaccines -
From Human Hemo Stem Cells and Auto/Alo Antigen-Presenting Cells 4) Take Tumor Samples 1) Whole Blood Pheresis 2) 9000 RPM Centrifuge with Carbohydrate Buffy-Coat takeoff 3) DynaBead Magnetic takeoff of CD2s & CD19s 5) Flourescent Activated Cell Sort Count 6) Proliferation of Dendritic Cells 7) Maturation

METHOD FOR STIMULATING AN IMMUNE RESPONSE

This application is a continuation of U.S. patent application Ser. No. 09/017,842, filed Feb. 3, 1998, now U.S. Pat. No. 6,251,665, issued Jun. 26, 2001, which claims the benefit of U.S. Provisional Application No. 60/042,110 filed Mar. 26, 1997, No. 60/038,736 filed Feb. 14, 1997, and No. 60/037,435 filed Feb. 7, 1997. The present invention relates generally to stimulation of hematopoietic progenitor cells of blood and bone marrow origin for the purpose of eliciting cell differentiation. More specifically, this invention relates to methodologies for specifically channeling the differentiation process of hematopoietic stem cells into Dendritic Cells (DCs) and particularly, specifically causing the differentiation of the hematopoietic cells into DCs so that they become Programmable Antigen Presenting Cells (pAPCs) having the capacity to direct a complete and/or specific immune response to a variety of targeted markers encoded by tumor RNA which markers are presented to the pAPC creating a Programmed Super-Presenting Cell (pSAPC) which subsequently may provide a treatment for specific disease states.

FIELD OF THE INVENTION

BACKGROUND

In recent years there have been numerous advances in the level of understanding of how cancer cells grow inside a host. Generally, it is known that where a tumor or cancer becomes manifest, either there is a deficiency in the host's immune system and/or the tumor cells secrete or express agents which block the normal response of the host's immune system. In any event, there is a failure on the part of the host's immune system to recognize the presence of the cancer cell as "non-self". Because of this failure, the tumor cell and its progeny are allowed to grow without the benefit of predatory attack from the host's immune system cells which are normally responsible for detection of abnormal conditions. Primarily, the immune cells responsible for such predatory attack are the white blood cells of the CD34 lineage including the lymphocyte-activated killer macrophages and the T8 killer cells. Cells derived from CD34 lineage naturally become differentiated to ten or more mature cell types dedicated to specific functions. The functionality is believed to be determined by factors, such as cytokines, leading to the next differentiated stage.

Although seemingly much is known of specific hematopoietic cells which have become differentiated into identifiable discrete cell types, little is known about the physiologic control mechanisms involved in such differentiation process. Thus, contemporary research has centered primarily on examination of specifically known cell types and the cell surface "markers" recognizable at each such differentiation stage. Conspicuously lacking in the art has been clearly useful information or understanding of physiological events taking place within the cells as they metamorphosized from one state to the next differentiated state.

Consistent with the current state of understanding such cell differentiation is the methodology utilized by leading physicians and researchers in treatment protocols for cancerous diseases. Over the past several decades, cancer treatment methodologies have centered on conventional therapies such as surgical excision, radiation, and the injection of potent chemical agents. Such methodologies have well recognized limitations and have, in many cases, been proved to cause much additional pain and suffering to the patient as well as unreliable long-term effectiveness.

Numerous recent treatments have attempted to affect tumor cells by direct manipulation of cells understood to be active in clearing the body of dead or improperly functioning cells. Understandably, the cells targeted for investigation have involved cells of the immune response system. However, recent attempts at blocking growth of tumor cells, though utilizing sophisticated methodologies (such as by attempting to block the immune suppression capacity of the tumor cells) have generally been unsuccessful. These attempts are still ongoing and are also of questionable benefit in bringing about reliable treatments resulting in long-term tumor remission.

Examples of methodologies in the recent art include targeted radiation and chemotherapy, injection of cytokines, injection of monoclonal antibodies to specific known tumor cell surface markers, and genetic therapies involving transforming cells with genes encoding factors believed to affect specific tumor states. One methodology has involved utilizing a class of natural immunostimulatory agents, particularly lymphokines, which are known to act as immunomodulators. Some lymphokines are produced by one T lymphocyte but act by signaling other T lymphocytes. Prior attempts have been disclosed in the art to regulate such immunomodulators by adding factors, such as Interleukin 2 (IL-2), to enhance or elicit an immune response to tumor cells and thereby trump the immunosuppression effect that many tumor cells exhibit. The difficulty with such past investigations directed at blocking immunosuppression is that they have either failed entirely or have only attacked specific antigenic markers produced by the tumor cells. Other methods of treatment have included direct injections of various cytokines. Still other methods have attempted stimulating the patient's immune response cells using cytokines in the presence of the patient's own cancer cells, then reinjecting the treated immune response cells. A number of attempts have been made along these lines and a significant percentage of the patients do not respond optimally to such interventions.

The results of treatments utilizing any of the above methods indicate that subpopulations of cancerous cells remain undetected and unaffected and are able to present later clinical manifestation of the cancerous state. For example, a number of very malignant cancers, such as glioblastoma multiforme, continue to be a death sentence prognosis for patients who are so afflicted. Virtually all patients relapse, even after conventional debulking, chemotherapy and radiation therapy. Typical survival after diagnosis is usually 18 months.

Other regiments include gene therapy. For example, when TGF-β detection gene is inserted into a host's tumor cells in vitro, then injected to attempt to elicit an immune response, treatments are only temporarily successful and fail to provide a lasting benefit, even when combined with IL-2 co-stimulatory regimens. The temporary effect results because not all of the tumorous cells have been eliminated. This is because populations of tumor cells are heterogeneous in the variety of surface markers they present. Not all such markers will be available for presentation to cells responding to the protective response effects of TGF-β or IL-2. Thus, some cells are not properly recognized in the treatment regime and survive undetected.

There is therefore an ongoing need for a means of stimulating more effectively and completely the host's immune response to serious disease and cancer states. The current invention has centered on the recognition that dendritic cells derived from precursor CD34+ and CD34− stem cells may be specifically directed to become a programmable antigen presenting cells (pAPCs). The current invention shows that in fact the pAPCs may indeed be programmed to become programmed super antigen presenting cells (pSAPCs) having the capacity to elicit an immune response to any number of tumor antigen moieties after being "loaded" with either tumor derived RNA in toto or the poly A+ population thereof, or with the expressed proteins encoded by such RNAs including immune significant tumor antigens expressed therefrom.

It will be well appreciated in the hemopoietic cell art that dendritic cells are typically bone marrow-derived leukocytes which are known to play a central role in cellular immune responses. There are many aspects of dendritic cell ontogeny which remain poorly defined. However, most studies suggest that these dendritic cells emerge from the bone marrow, circulate in the peripheral blood in an immature form, and then enter tissues where they function as antigen-presenting cells or differentiate into macrophages. Once these dendritic cells capture a foreign body or some type of cell recognized as non-self, they then migrate to central lymphoid organs where they present these antigens to the T lymphocytes. Once the dendritic cell makes the presentation to the T lymphocytes, the T lymphocytes then mount an immune response.

Dendritic cells are difficult to study due to the scarcity of their populations and difficulty in growing these cells in cell culture. Dendritic cells can be derived from three readily available sources: (1) peripheral blood monocytes, (2) bone marrow and (3) umbilical cord blood. The functional differences between dendritic cells which are derived from the peripheral blood monocytes and those derived from bone marrow remain controversial. Dendritic cells possess ideal characteristics to be used as antigen-presenting cells. The key problems experienced by researchers has been both the inability to retrieve dendritic cells in sufficient quantity and to direct a stem cell to develop into a dendritic cell either in sufficient quantity or sufficient specificity. Therefore, if dendritic cells could be properly propagated and channeled, the fact dendritic cells possess ideal characteristics to generate a tumor-specific cellular immune response by processing and presenting tumor-associated antigens to primed CD4+ T lymphocytes, dendritic cells would offer a highly desirable and efficient means to initiate an immune response.

Moreover, the current state of the art in cancer research has focused on the science of recombinant DNA sequencing. In general, researchers are searching the genomes of cells for DNA sequences encoding genes responsible for causing either the cancerous state itself, or the cancer's immunosuppressive effects. At least 6,000 genes have been identified and characterized. The human genome itself is estimated to harbor at least 100,000 genes. Additionally, it is believed that any given cell may express 20 to 45 thousand different genes during its life cycle, if not at one time. Cancer cells are believed to express numerous genes in addition to, or in lieu of, those normally expressed and in fact may express a greater number than the average normal cell.

Previously, researchers have focused on identifying various unique genes such as Her2neu or Brac-a, and have associated such specific genes with specific cancers. Unfortunately, by focusing on single genes so associated with a cancer, the possibility that such genes may have little significance with respect to an immunological response greatly increases. The reason that such single genes may not be all important to the cancer state and immune response is that such cancer cells are heterologous, not homologous, with respect to expression of surface antigen markers.

The present invention furthers the state of the art by making it clear that it is not significant to identify every single gene that is expressed on a cancer cells. Rather, that it is important to provide a means by which the expressed genes of a cancer cell may be presented along with, or in combination to, the immune response system by a means directly useful to the "natural" mechanisms of recognition utilized by immune system cells. The inventors of the present invention delineate how this may be accomplished by directed growth of dendritic cells to a state where they may become programmable antigen-presenting cells (pAPCs), capable of digesting a foreign cell (non-self), or ingesting foreign cell RNA in toto or as the poly A+ portion thereof, or the expression product encoded by such RNAs. The inventors intend for the pAPCs to select appropriate cancer RNA or RNA expression products to be most appropriate for presentation.

Although a similar digestion of nonself matter occurs in the natural setting with the aid of macrophages and other phagocytotic cells, the present invention avoids the conditions understood to occur in vivo and accomplishes enhanced digestion and presentation in vitro. The current invention provides for uniform conditions under which dendritic cells may be directed or evolved to a state where they may be highly effective in digesting and/or selecting appropriate cancer and other cell markers for presentation. The inventors hereby suggest that during the digestion process, the dendritic cell will itself identify those antigens of significance for the immune system meaning that it will select out some 10 to 20 or more antigens from a specific cancer cell, RNA, or RNA encoded product which have immunological significance. Under in vivo conditions of a host afflicted with a cancer, such selection may not be effectively recognized by the immune system, especially one that is compromised or masked. In contrast, under conditions of the current invention, the dendritic cell selected markers may be presented to T4 and T8 cells in an environment which will allow such T4 and T8 cells to become properly educated and activated so as to trigger a useful immune response.

The current invention provides a means by which the dendritic cell can be activated to become a "programmable" antigen-presenting cell or pAPC which is a "manufactured" dendritic cell line and which can further be "immortalized". Immortalization of the pAPC allows for a suitable continuous source of cells which may comprise the basis of an allogenic vaccine. Therefore, the donor host or any host of the same allotype with the same disease, exhibiting such RNA in toto or poly A+ portion thereof, or the encoded protein therefrom, with this source of allogenic dendritic cells will create vaccines directed to particular tumors. Similarly, these allogenic dendritic cells may be mixed with representative samples of different tumors' RNAs or RNA encoded products. For instance, the current invention contemplates combining a plurality of tumor's RNAs and/or RNA expression products from progressive stages of the same cancer type. By representing differentiation periods in the disease state progression, a heterogeneous population of tumor cell antigens are presented to the pAPC and therefore a single vaccine may be created representing "different phases" of the cancer giving rise to a multivalent vaccine. Therefore, one vaccination using such an allogenic-based vaccine may protect against the whole spectrum of a specified cancer. Similarly, an allogenic vaccine for one very poorly differentiated cancer with many atypical features may also have an effect on more early stages of the same type of cancer or a different cancer, meaning that a vaccine made from allogenic pAPCs to glioblastoma tumor tissue, or its RNA, or its RNA expression products for instance, may prove efficacious in use with other unrelated tumors such as a prostate cancer. The current invention further provides for "commonalities" between all cancers which makes possible a single allogenic vaccine that is effective for a multiple of different cancers. Thus, many features which are similar to all cancers may be provided for in a pSPAC for presentation to cells of the immune system, in effect providing immune-specific antigens with commonality between different tissue types.

The current invention also contemplates use in placing specific antigens on the pAPC which function in a regulatory surveillance mode to prevent recurrence of a new cancer or a heterozygous group of cancer cells from growing out of control. For example, a pAPC "programmed" for lung cancer may be used in effectively eliminating a host's cancer using an "autogenic" lung cancer vaccine. Where a subgroup of cells survive this immune response, because a heterozygous group of antigens is not recognized as that presented by the pSAPC, a different pSAPC with "memory" to capture di novo cancers may also be used to educate immune system cells. Such pSAPCs equipped with "surveillance antigens" may be effective not only against a heterozygous group of tumor antigens but may also be used for surveillance in di novo cancers separate from the original cancer for which the host was treated using the autogenic vaccine.

SUMMARY OF THE INVENTION

It is therefore an object of the present invention to provide a method for stimulating a directed immune response in cells of a living organism. More specifically, it is an object of the invention to provide a means for stimulating immune response in cells of a mammal, and particularly of a human, by isolation, separation, and propagation of precursor DCs in high yield from the blood and marrow of patients afflicted with cancer. It is a further object of the invention that this means provide for predetermining the evolution of precursor cells into programmable antigen presenting cells suitable for presentation by mixing to preselected antigens to elicit a host immune response capable of recognizing any or all expressed markers of tumorous cells or any other "non-self" tumorous cells or RNA of said tumor cells, or expression products encoded by such RNAs, or other nonself antigens. The invention further contemplates a process for aiding treatment of both early and terminal stages of cancer and other infections and diseases.

A primary object of the invention is to provide a method of preventing, treating, reducing the severity, or possibly curing a disease in the subject by stimulating the subject's immune response against the disease. The scope of the invention further contemplates providing treatment methodology for the whole spectrum of human diseases the successful treatments of which rely on stimulation of the immune system for fighting infections and cancerous states.

Another object of the invention is using pAPCs in treating solid tumors via a protocol wherein pSAPCs derived from pAPCs act as vaccines. Yet other specific objects of the invention include adding cancer cell RNA and RNA expression products directly into a pAPC whereby the protein antigens encoded by such RNA can be expressed on the surface of the pSAPC. Another embodiment of the invention contemplates extracting tumor RNA, cloning such RNA into bacterial expression vectors, then transforming the pAPCs with said vectors so that tumor gene products may be directly propagated in the pAPC for high level presentation by the pAPC to induce a specific immune response.

The invention further contemplates the creation of a vaccine to specific cancers including lung, prostrate, and breast cancers. Moreover, a preferred embodiment of the invention contemplates the creation of allovaccines which can be created by donor DCs adhering to the nine basic MHC-I and MHC-II phenotypes. Such allovaccines are further contemplated to include the immortalization of the nine DC lines known to derive from precursor CD 34 stem cells utilizing currently well characterized Epstein-Barr virus and other immortalization techniques (such as by retro and adenoviruses) understood by those skilled in the art. This embodiment contemplates that the immortalized allogenic DCs will be "loaded" with specific cancer cells, or RNA in toto or the poly A+ portion thereof, or gene products thereof, or bacterial expression vectors containing tumor cell genes derived from said RNA thereof, followed by mixing the treated DCs with a host's plasmaphoresed T4 and/or T8 cells which mixture or resegregated cells (T4, T8, or pSAPC) would then be returned to the host's system to induce the desired lasting immune response to the specified antigens and cancer cell markers.

The present invention provides for a method of extracting and separating precursor DCS from the blood of a mammal. A preferred embodiment contemplates extracting and separating a subject host presenting a diseased state the treatment of which requires host immunomodulation. The invention contemplates plasmaphoresing the blood to separate and isolate CD34+ and/or CD34-lineaged cells. In another preferred embodiment, bone marrow cells may be used in place of fresh whole blood. The isolated cells are then incubated with a specific regimen of treatments heretofore not appreciated in the art to create an antigen-presenting DC. The steps of creating the antigen-presenting DCs utilize an in vitro process to exclusively yield activated dendritic cells which can then be presented with a host's disease state tumor cell or component parts or constructs thereof as previously described. The DCs thus activated are termed pSAPCs.

The invention contemplates generation of both autogenous pAPCs and allogenic pAPCs. Allogenic pAPC vaccines are created using the nine DC phenotypes based on the known histocompatibility complex antigens (MHC I and MHC II). Both autogenous and allogenic pAPCs may be "programmed" to any one or combination of such antigens. Programmed presenting cells (pSAPCs) are capable of eliciting "upgraded" cellular antitumor responses in the host's T lymphocytes population via MHC class I and II pathways acting in association with accessory and adhesion molecules, such as B7-1, B7-2, and ICAM-1. The endocytic activities of these pathways are marked by a capacity to vigorously ingest fluid phase and whole cell lysates by macropinocytosis, and in turn deliver ingested solutes to prelysosomal MHC class II-rich vesicles for subsequent presentation as MHC class II surface molecules. The specific and channeled use of the DCs according to the present invention avoids the natural activity of the T lymphocyte's response to a tumor cell which treatment regiments known in the art presently utilize. In such regiments, the T lymphocyte must locate the antigen directly from the host's blood fluids or from the surface of the tumor itself. Thus, the T lymphocyte has only the chance to respond to antigens it can find, without the aid of highly activated programmed DCs, allowing for the tumor cell to evade immune surveillance either due to poor immunogenicity, or lack of the presence of a recognizable surface antigen. In contrast, the pAPC of the current invention are capable of "digesting" a tumor, or its RNA, or expression products of such RNA, selecting suitable antigens so derived from the tumor, and expressing the antigens on the surface of the pAPC for presentation to other cells of the immune system either in vitro or in vivo.

A preferred embodiment of the invention contemplates utilizing the pAPCs as effective autogenic and allogenic vaccines and boosters against tumor antigens and cell markers in vitro or in vivo. Moreover, since the pAPCs have the capacity to become immortalized, the current invention contemplates creating banks of immortalized cells comprising activated pAPCs for use as allogenic vaccines and boosters.

The invention further contemplates mixing the pSAPCs with a host's CD4+ T helper cells and CD8+ T killer cells which are isolated from whole blood or bone marrow. Such mixing under conditions of the present invention allows the antigens on the surface of the pSAPCs to be presented to the T cells, which presentation allows the T cells to become sensitized to the cancer-specific antigens. It is well-known in the art that such cancer-specific T lymphocytes are capable of mediating effective immune surveillance against subsequent manifestation of the specific cancer. Thus, once "activated" as described herein, the CD4+ T helpers and CD8+ T killer cells can be utilized as effective autogenic vaccines and boosters upon reinjection into the subject host, having been treated for activation according to the presently described and heretofore unrecognized method.

The mechanism of stimulation of the T cell is believed to occur according to the following description. First, naive CD4+ T cells when stimulated via presentation to the pAPC produced MHC class II antigens, become "educated" and initially produce IL-2. Next, they develop either into educated TH1 or educated Th2 cells, depending on the specific regiment utilized to produce the pAPC including the nature of cytokine regulation utilized, type of antigen presenting cell used, and the expression of accessory molecules of such cells. It is known that Th1 cells produce IFN-γ, TNF-β and IL-2, while Th2 cells are known to produce IL-4, IL-6, and IL-10. There are cross-regulatory effects between Th1 and Th2 cells mediated by the cytokines in the form of cross-cytokinic stimulation and inhibition. For instance, IL-4 inhibits the development of IFN-γ producing cells while dysregulated IL-10 production normally serves to limit Th1 lymphocyte response.

The DC programming technique of the present invention uses the host's dendritic cells derived from CD34+ and CD34− cells to create programmable antigen-presenting DCs which are used in turn to stimulate activation of cytotoxic T-4 helper lymphocytes. The T-4 helpers in turn activate T-8 killer lymphocytes which attack tumor cells directly. The DCs ingest fluid phase-nonbinding antigens from whole cell lysates, or such cells' RNA, or expression product of said RNA. The DCs may also be transformed with bacterial expression plasmids containing tumor cell cDNA. Once the DC has ingested said tumor antigens or has expressed tumor RNA, such antigens and expressed products are exocytosed after being processed by prelysomal MHC-I and MHC-II vesicles. From these prelysomal vesicles various antigens of the host's tumor cells are transmitted to the surface of the now superpresenting pSAPC. The pSAPCs elicit effective antitumoral responses by presenting antigens to T-cell lymphocytes via MHC class I and MHC class II pathways as well as expressing necessary accessory and adhesion molecules such as ICAM-1, B7-1, and B7-2.

Another preferred embodiment of the invention contemplates taking advantage of the pAPC's prolific expression of adhesion and accessory surface molecules and the responsiveness of T-lymphocytes to the pAPC presented antigens which responsiveness is overpowering compared to the previously evasive detection experienced by other immune stimulation protocols.

Yet another embodiment of the invention contemplates use of the successful activation and population expansion of tumor-specific T-4 and T-8 lymphocytes (utilizing phoresed lymphocytes in vitro) to provide a means of boosting old antergized T-cell populations.

As is understandable to those skilled in the art, the tumoral masking and successful camouflaging experienced in past treatment protocols due to anti-Th1 measures of contra-IL-10, IFN-gamma, and TGF-β are overcome by the pAPC of the present invention. Moreover, the present invention may also circumvent the temporary nature of enhanced solid tumor immunogenicity obtained in gene insertion/deletion therapies of IL-2/TGF-β caused by B7 and ICAM I or the interference from CD28/CTLA-4 and LFA-1, or effects of B7 on induction of INF-gamma. By co-incubation of pAPCs with the host's tumor cells, with subsequent incubation with host T cells, the resulting antigens displayed and immunogenic response to be observed is profound.

The DC programming technique of the present invention further contemplates utilizing RNA from cancer cells that have already been excised from patients and either maintained in frozen preservation or preserved in paraffin cell blocks used for histology analysis. Thus, with this invention, one need only take surgical tumor specimens by invasive means on one occasion. The material preserved in paraffin blocks may be de-paraffinated by standard laboratory techniques and the messenger RNA from the tumor cells extracted. Whether from frozen stock or paraffin block, this RNA, which includes the cell's mRNA, may then be used for direct incorporation into the dendritic cells or, may be used through standard in vitro expression methods to obtain encoded mRNA expression products for direct incorporation into the DC, or may be reverse transcribed into cDNA and cloned into bacterial expression vectors for transformation of the Dcs.

BRIEF DESCRIPTION OF THE DRAWINGS

The foregoing and other objects or features and advantages of the invention will be made apparent from the following detailed description of the preferred embodiments of the invention and from the drawings in which.

DETAILED DESCRIPTION

It will be appreciated by those skilled in the art that immunogenic potential exists in most human blast cells and that precursor B lymphoblasts present tumor and MHC-associated antigens. This presentation is well-known to elicit specific T lymphocyte response to such antigens. A primary embodiment of the current invention rests on the inescapable conclusion to be drawn from the T lymphocyte response to B lymphoblast antigen presentation that human dendritic cells if primed by coculturing them with autologous lymphoblasts, or whole cell lysates therefrom, or their RNA in toto, or the poly A+ portion thereof, or expression products of such RNA therefrom, or are transformed with expression vectors containing cDNA thereof, will also act in presenting antigen to T lymphocytes. Recent strategies to stimulate the development of tumor specific T lymphocyte responses have utilized professional antigen presenting cells, including dendritic cells, to elicit effective cellular antitumor responses by presenting antigens to T lymphocytes. This presentation and response is attributable to the professional antigen presenting cell's ability to process antigens via the MHC class I and II pathways in association with accessory and adhesion molecules, including B-7, B7-21 and ICAM-1 which are necessary to ensure a T lymphocyte response for the reason that tumor cell immunogenicity is often poor. In the current invention, DCs are utilized for their antigen presenting properties and ability to prime naive CD4T-helper cells via MHC class I and II CD8+ cytotoxic T lymphocytes (CTL) directly. DCs have the ability to vigorously ingest nonbinding antigens, such as whole cell lysates, and further have the ability to deliver bits and pieces of such lysates, or their RNA in toto, or transcribed poly A+, or proteins encoded by such RNA, to MHC class II-rich vesicles for incorporation into peptides prior to display on cell membranes as MHC class II surface molecules.

The mechanism of the current invention differs from prior vaccine preparation processes in that DCs of the present protocol are primed with lymphoblasts prepared as either whole cell lysates, isolated RNA, expressed RNA gene product, or expression vector containing reverse transcribed mRNA, rather than a derived lymphokine peptide and/or whole intact tumor cell. This approach is taken for two reasons. First, expression of individual antigen markers in prior research has proven ineffective. Second, the use of autologous tumor cell lysates will provide simultaneous immunization against all markers present in the host's tumors, and thus avoid selection of resistant lymphoblast antigen-loss variants. Moreover, not only does the whole cell lysate method avoid antergy, it also avoids the masking effect that some tumors exhibit. In a preferred embodiment, this invention focuses on priming DCs at an early stage in their maturation cycle when antigen capture exhibits greatest potential. Recognition of this aspect of cell response activity is an important part of the success experienced by this invention. Thus, the methodology of the current invention for eliciting response in lymphoblasts insures a "shotgun" response. In contrast, prior research has centered on singly identified antigenic moieties which have had the potential of responding to only one type of antigen being "expressed" while missing other surface expression molecules. The prior research therefore provides for selection of only a subpopulation of tumor cells while missing others. Understandably, recurrence of tumor tissues may occur within a few months. This is why gene therapy is successful at first but subsequently shows disappointing results after several months.

Figure 1:
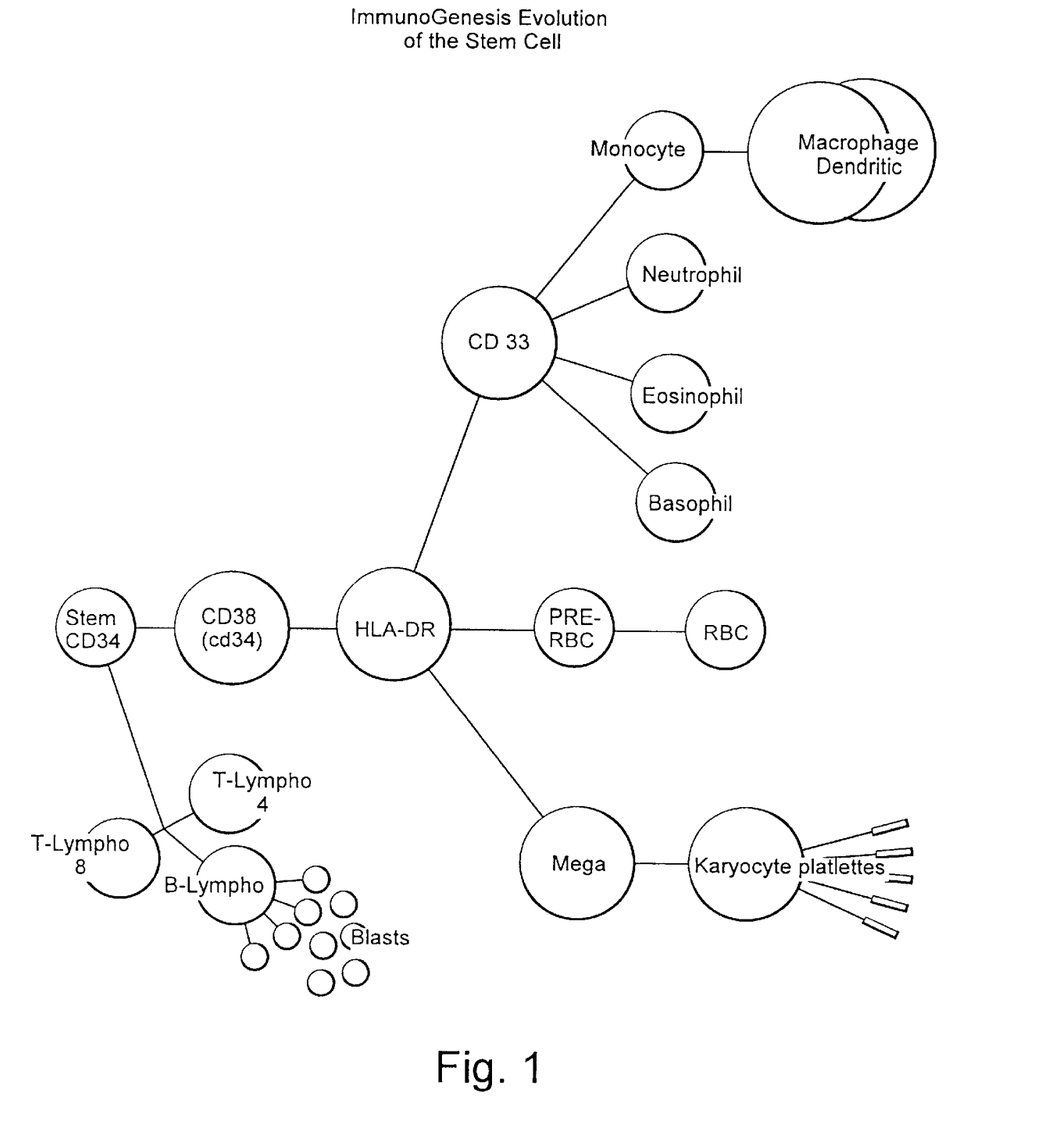
FIG. 1 is a schematic chart indicating the cell differentiation lineage of hematopoietic cells indicating the evolution channel of stem cells.
Figure 2:
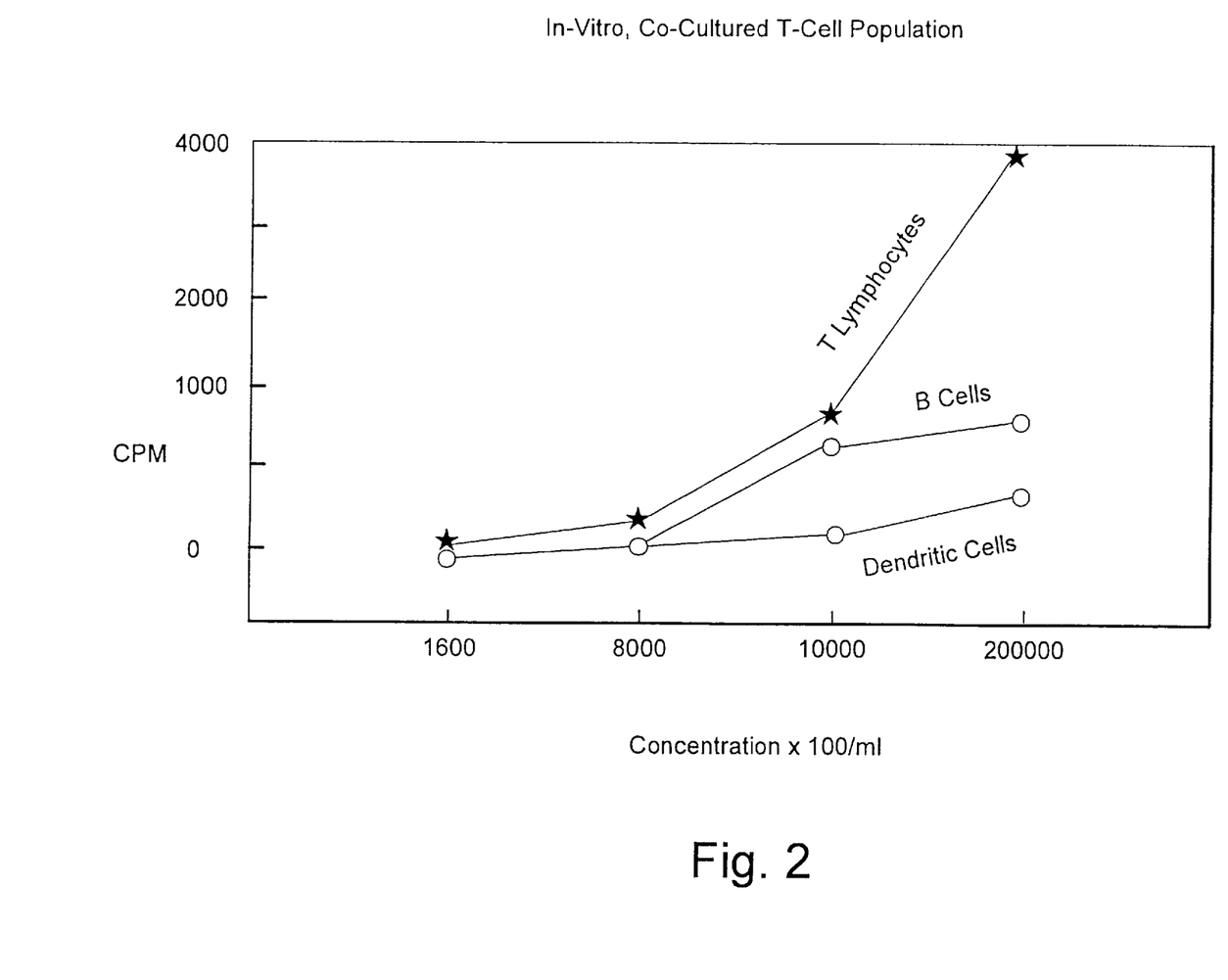
FIG. 2 is a graph showing results of proliferation assay on "loaded" T lymphocytes of human DCs programmed and grown from base stock of autologous CD34+ HPC from peripheral blood, cultured with GM-CSF, IL-4 and TNF-χ.
Figure 3:
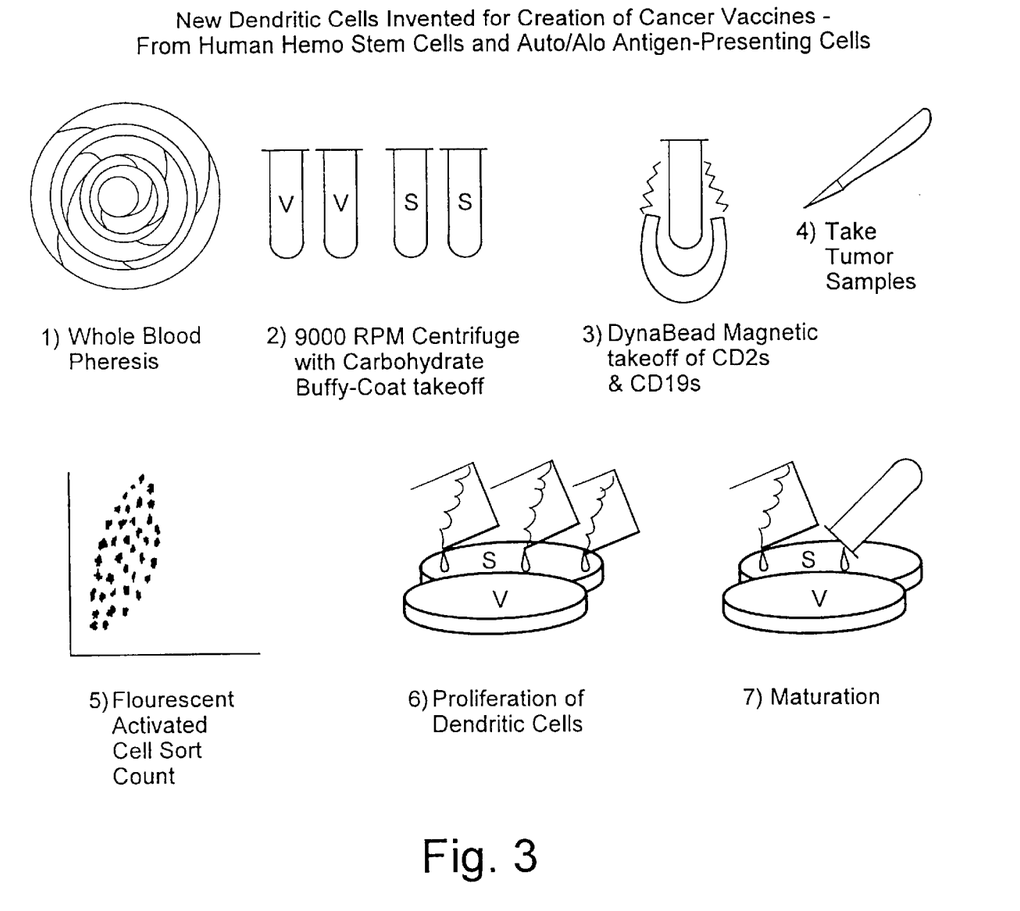
FIG. 3 is a pictorial chart delineating progressive steps to be taken in stimulating CD34 cells to create antigen-presenting DCs.
Figure 4:
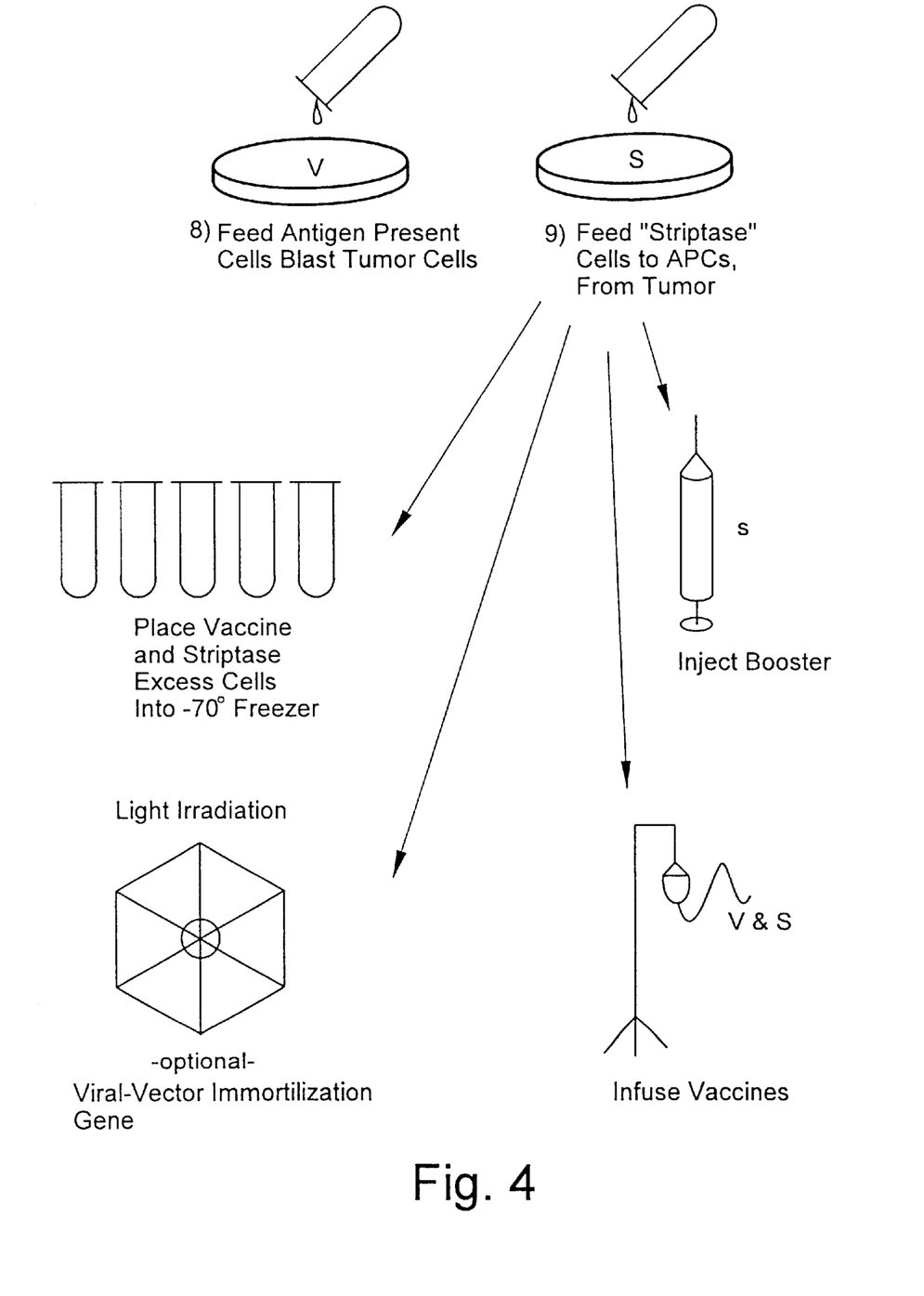
FIG. 4 is a pictorial chart delineating basic steps to create programmed pAPCs, activated T cells, and the subsequent methods of administration of such pAPC/T cell mixture to a subject host.

According to the preferred objects of the invention, and referring generally to FIGS. 1, 3 and 4, the steps necessary to direct CD34+ and CD34– stem cell to become a super antigen presenting cell include the following general outline. (First, FIG. 1 shows the cell differentiation lineage of hematopoietic cells. The protocol of the present invention directs CD34+ and CD34-cells to antigen-presenting dendritic cells. Peripheral whole blood or bone marrow cells are cultured in the presence of SCF, GM-CSF, IL-4, and TNF-χ. The resulting cell population comprises antigen presenting DCs which are programmable with any antigen engulfed by them. These cells may also be referred to as pAPCs. The cells are then "loaded" or "programmed" using irradiated whole cell lysates, cell RNA or the poly A+ portion thereof, or expression products of cell RNA or transcribed RNA, or cDNA of cell mRNA, or plasmid expression vectors containing such cDNA, of autologous lymphoblasts. Programmed DCs are used as T lymphocyte stimulator cells while a small portion is reserved in cytopreservation. After addition of the T lymphocytes in the presence of TNF-χ, proliferation of T lymphocytes is then measured by 3H-thymidine uptake. As shown in FIG. 2, the T lymphocytes are dramatically stimulated to proliferate.

In the aforementioned protocol, stem cell factor is used to expand the pool of hematopoietic progenitor cells, GM-CSF is utilized to promote the growth and maturation of dendritic cells, IL-4 is used to suppress overgrowth by macrophages, and TNF-χ, is added after about 5 days in culture to facilitate maturation of DCs. The culture is then propagated to create an autologous vaccine comprising antigen presenting dendritic cells.

EXAMPLE I (CD34+)

The preparation of pSAPCs by directing the maturation of CD34+ cells is similar to the methodology used to direct CD34– cells. However there are distinct protocol differences. For CD34+ directed maturation host peripheral blood is ficolled, washed and resuspended in PBS/0.1% BSA. The cell suspension, consisting of "adherent" (monocytes and macrophages) and "nonadherent" (stem cells, T4, T8 and B cells) are separated such that the nonadherent cell types are retained. This nonadherent mixture is then reacted with Dynal magnetic beads (indirect) which are sensitive for T4, T8 and B cells. The stem cells from which pAPCs will be generated are left in solution. The beads are then centrifuged and cells in solution are stained using directly conjugated FITC and PE-labeled CD3, CD19, CD34, CD14, CD45. The stained cell suspension is then analyzed by flow cytometry. Desired fractions are collected and cultured in AIM 5 (made by Gibco) in 10% FBS, 10% HS, 1% NEAA, 1% NaPyruvate, 1 Pen/Strep+800 U/ml GM-CSF, 500 U/ml IL-4, and 20 mg/ml SCF at 37° C. in 5% CO2. The cells are cultured for 4 to 6 days according to standard suspension culture protocols. Cytopreparations are obtained and stained with Wright's/Giemsa for flow cytometric analysis every four days during culture. The cells are examined for the following: CD2, CD13, CD14, CD19, CD34, CD45, CD80, CD86, CD1a, HLA-1 and HLA-DR. The dendritic cells are then pulsed with any one or combination of the following: 1) "foreign" (tumor) cell RNA in toto, 2) foreign poly A+ RNA, 3) expression product of foreign mRNA, 4) expression plasmid containing cDNA from tumor cells, after which growth media is added for a concentration of $2 \times 10^6$ cells/ml for 72 hour coculture at a concentration equivalent to a 1:1 lymphoblast to dendritic cell ratio. These loaded dendritic cells are then cryopreserved or used immediately as T lymphocyte activation cells.

Where whole tumor lysate tissue is to be added to the DCs, the lysate is treated with standard rapid freeze thaw method then irradiated with up to 40 Gy gamma source to insure that there is no viable cell or nucleic acid. Otherwise the RNA isolated by standard methodologies and either used in toto or fractionated to isolate the poly A+ fraction. The RNA, either in toto or as poly A+, is then either added directly to the DCs, translated using standard in vitro methodologies and the expression products with the RNA added to the DCs, or is reverse transcribed into cDNA, cloned into an expression vector and then transformed into the DCs by standard techniques. Regardless of the treatment of the RNA or cell lysate, such material is presented to the pAPCs approximately 4 to 7 days after initial culture of the DCs. The pAPCs are retreated with lysate or RNA derived material as above described again at about day 10 and at about day 15 from initial culture of the dendritic cells.

Following maturation of the cells as described in the above steps, T4 helper leukocytes and T8 killer leukocytes are added to the pSAPC/tumor cell culture and allowed to incubate for about 5 days. Importantly, the morphology of the T cell pool is examined to ensure that they are not in a presently excited or activated state. Such state is recognizable by the increased size normally associated with activated state T4 and T8 cells. If the morphology indicates that the cells are activated, they are first allowed to return to an ambient state prior to introduction to the DCs. The T4/T8 pool is added at about a 1:1 ratio of T4/T8 to pAPC. Following this incubation period, the cell culture is again subjected to fall flow cytometry analysis for separation and isolation of the T4 and T8 cells. Depending upon the proliferation count, the T cell pool and/or dendritic cell populations may be introduced into the host. Where the T cell count has not reached satisfactory levels, the cells may be introduced to the pSAPCs for further culture. Moreover, the T cells may be reintroduced where T cell/dendritic cell populations have reached satisfactory levels for the purpose of hypersensitizing them to the desired antigens. Where restimulation of T cells by pSAPC is contemplated, it is preferred to allow the educated T cell pool to return to an ambient state. Besides adding the T cell pool to the host alone, these cells may be introduced to the host in conjunction with the pSAPC. Moreover, the pSAPCs may be introduced to the host alone. Whether introduction to the host is by T cells alone, T cells plus pAPCs, or pAPCs alone, the fraction(s) are presented to the host system for eliciting sustained immune response (i.e., memory).

EXAMPLE II (CD34−)

The ability of utilizing the potential of CD34− cells provides for marked improvement to current methodologies known in the art. It is known that peripheral blood contains up to approximately a ten to one ratio of CD34− to CD34+ cells. Use of CD34− cells provides for a vast increase in cell population that can be effectively utilized in cancer therapy regimens. Moreover, the difficulties associated with leukophoresis procedure currently carried out to obtain sufficient quantities of stem cells will be avoided. Currently CD34− cells are discarded as it is believed that they are precommitted to become macrophages. However, CD34− cells may be programmed towards dendritic commitment with proper incubation and lymphokine stimulation.

In this example, the cell donor is pretreated with IL-3 and either G-CSF or GM-CSF. For adult patient/donors, the regimen is administration of IL-3 at 15–55 ug/Kg/day for 4 consecutive days followed by 3 days without such administration. Next, either G-CSF or GM-CSF is administered at 15–55 ag/Kg/day for 5 days followed by 2 days of blood retrieval from the donor/patient of 50 to 90 ml of venous blood drawn each day. Blood is drawn in heparinized syringes. Such pretreatment may yield a higher number of CD34+ and CD34− cells up to 40× multiple of progenitor cells over that normally found in peripheral blood. After the pretreatment period, blood is removed from the donor and the white blood cells are removed by standard protocol. Following magnetic bead separation as described above in example 1, the stem cells containing CD34+ and CD34− cell populations are washed in PBS containing 1% human autologous plasma four times by standard laboratory techniques. The cells are then cultured in RPMI 1640 culture medium containing 1.0% heparinized autologous human plasma, 10 mM Hepes, 20 ug/ml Gentamicine, 1×105 U/ug rhGM-CSF (Kirin), and 0.5×105 U/ug rhIL-4 (Immunex). The culture is allowed to incubate in the above media for 7 days at 37° C. during which the cells are replenished every other day with fresh media and lymphokines. This process of in vitro incubation allows the CD34− cell population to become immature dendritic cells. If cell populations have not reached adequate levels during this 7 day incubation, they may be allowed to grow an additional 7 days using the same growth media protocol. Moreover, following this protocol, the cells may be preserved in frozen culture at this stage.

After the above growth cycle, the non-adherent cells are collected by pouring off the growth media via moderately vigorous aspiration and transferred to fresh 6 well IG coated plates (Bacteriologic plates Falcon) in the following protocol. The plates are first washed with PBS followed by addition of 4 ml/plate of human gamma-globulin (Chappel Labs) at a concentration of 10 mg/ml for 1 minute. The plates are then washed 3 times in PBS. The stem cell population from above growth cycle are added to the IG plates at a concentration of $5 \times 10^7$ cells per well in a volume of 6 to 8 ml for 1 hour at room temperature. Following this incubation, the plates are washed to remove non-adherent cells by gentle aspiration and the remaining adherent cells are incubated for 3 days at 37° C. in medium containing 1.0% autologous plasma and SACS (fixed *staphylococcus aureus* 1/10,000 dilution), Pansorbin (Calbiochem) at a dilution of 1/10,000, 1640 RPMI, 10 mg/ml Hepes, and 20 ug/ml Gentamicine. From this cell mixture the immature CD34− cells are conditioned to become mature dendritic cells expressing among other receptors CD83 which is a co-receptor to T cell activation.

After the 3 day maturation cycle, the mature dendritic population are ready to be pulsed with tumor antigenic materials as described in example 1 to become pSAPCs followed by use in activating T and B cell populations.

A constant pitfall encountered in prior attempts at creating a dendritic vaccine was the dependence on the circulation in the peripheral blood of specific T lymphocytes generated in central lymphoid organs after the vaccine has been administered. This problem has been overcome by our "preprogramming" of precursor dendritics. Therefore, "traveling" through the body becomes programmed-in under our maturation process. Although a complete host immune response is anticipated, T4 or T8 response could be subnormal in some individuals as assayed by flow cytometry analysis. To cover this contingency, a small portion of phoresed blood components are set aside initially as a reserve in case initial treatment assays are below "par". Par is determined by standard multiparameter flow cytometry with monoclonal antibodies and fluorescent reagents. These assays at baseline and 30, 60, 90 and 120 days use standard cytotoxic T-lymphocyte limiting dilution assays. An additional reserve is set aside before the vaccine is infused into the host for the purpose of providing a source of booster material to be used at 30 and 60 days after initial infusion. These time intervals are chosen due to the production cycle of pAPCs being 21 days. Since the host's original irradiated tumor cells are phenotypically identified, the fact that they may not be clonogenic does not affect the host's pAPCs from expressing homologous associated effective MHC I and II class surface antigens.

It will be appreciated by those skilled in the art that the above protocol may be used with any of the known cancer or tumor disease states to detect, and propagate an immune response to antigens, receptors, ligands or other cellular components expressed by such cancer and tumor cells. Examples of cancer cell types and the identified diseases contemplated for use with the embodiments of the invention include: 1) that spectrum of disease states characterized by dysfunction of the T cell system such as psoriasis, eborrheic dermatitis and other skin diseases: 2) T cell lymphoma; 3) systemic acute autoimmune disease states such as rheumatoid arthritis and systemic lupus erythematosis; 4) organ specific antiimmune states such as Crohn's disease, multiple sclerosis, Guillain Barre' syndrome, Graves disease, pernicious anemia, Addison's disease and sarcoidosis; 5) HIV/AIDS wherein pAPC is targeted to infected T4 cells; 6) specific carcinomas such as adenocarcinoma of prostate, breast, colon, ovary, uterus, stomach, kidney and pancreas; 7) lung carcinoma of all histological types such as adenocarcinoma, squamous cell carcinoma, small cell carcinoma, large cell anaplastic carcinoma; 8) malignant brain tumors such as astrocytoma and glioblastoma multiforme; 9) urinary tract carcinoma including transitional cell, squamous cell, and adenocarcinoma; 10) squamous cell carcinoma of the esophagus; 11) infections such as bacterial, viral, and fungal.

Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims.

What is claimed:

1. A method of stimulating a disease-specific immune response, the method comprising infusing an immunogenic cell composition capable of stimulating a disease-specific immune response into a patient whereby a disease-specific immune response is initiated, the immunogenic cell composition being prepared by:

a) isolating hematopoietic stem cells from a donor;

b) incubating the stem cells in a cell culture medium comprising GM-CSF, SCE and IL-4, whereby the stem cells are directed to develop into programmable antigen presenting cells (pAPCs);

c) mixing the pAPCs with cellular material derived from cells positive for the disease, the cellular material selected from the group consisting of cell lysate, cell RNA, cell poly A+ RNA, cDNA derived from cell RNA, and cDNA derived from cell RNA incorporated into an expression vector;

d) incubating the pAPCs with the cellular material, whereby loaded pAPCs are produced; and e) incubating the pAPCs with TNF-α after the pAPCs have been loaded, whereby disease-specific programmed surer antigen presenting cells (pSAPCs) capable of stimulating an immune response to said disease are produced.

2. The method of claim 1 where the donor and the patient are one in the same.

3. The method of claim 1 where the donor and the patient are not one in the same.

4. The method of claim 1 wherein the hematopoietic stem cells are selected from the group consisting of:

a) CD34 positive hematopoietic stem cells; and b) CD34 negative hematopoietic stem cells.

5. The method of claim 4 wherein the donor is subject to a pre-treatment protocol with agents that increase the number of hematopoietic stem cells in the donor's peripheral blood, the pre-treatment protocol selected from the group consisting of:

a) IL-3 treatment for 4 consecutive days, followed by 3 days of no treatment, followed by GM-CSF treatment for 5 consecutive days; and b) IL-3 treatment for 4, consecutive days, followed by 3 days of no treatment, followed by G-CSF treatment for 5 consecutive days.

6. The method of claim 5 where the donor and the patient are one in the same.

7. The method of claim 5 where the donor and the patient are not one in the same.

* * * * *